(12) United States Patent
Hayakawa et al.

(10) Patent No.: US 8,574,557 B2
(45) Date of Patent: *Nov. 5, 2013

(54) COMPOSITION FOR A COSMETIC AND A COSMETIC COMPRISING THE SAME

(75) Inventors: Chihiro Hayakawa, Tokyo (JP); Hiromasa Yamaguchi, Takasaki (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 101 days.

This patent is subject to a terminal disclaimer.

(21) Appl. No.: 13/039,513

(22) Filed: Mar. 3, 2011

(65) Prior Publication Data

US 2011/0217250 A1    Sep. 8, 2011

(30) Foreign Application Priority Data

Mar. 5, 2010 (JP) .................................. 2010-49644

(51) Int. Cl.
*A61K 8/81* (2006.01)
*A61K 31/00* (2006.01)
*A61K 8/00* (2006.01)

(52) U.S. Cl.
USPC .............................. 424/59; 424/78.3; 424/64

(58) Field of Classification Search
USPC .......................................... 424/64, 59, 78.03
See application file for complete search history.

(56) References Cited

U.S. PATENT DOCUMENTS

| | | | | |
|---|---|---|---|---|
| 4,340,709 A | * | 7/1982 | Jeram et al. | 528/15 |
| 4,987,169 A | * | 1/1991 | Kuwata et al. | 524/267 |
| 5,266,321 A | * | 11/1993 | Shukuzaki et al. | 424/401 |
| 6,235,292 B1 | | 5/2001 | Bara et al. | |
| 6,747,115 B2 | | 6/2004 | Sakuta | |
| 2002/0058053 A1 | | 5/2002 | Nakanishi et al. | |
| 2004/0147670 A1 | | 7/2004 | Hupfield | |
| 2008/0311060 A1 | | 12/2008 | Sakuta et al. | |

FOREIGN PATENT DOCUMENTS

| | | |
|---|---|---|
| EP | 2363425 A1 | 9/2011 |
| JP | 6-55897 B2 | 7/1994 |
| JP | 8-6035 B2 | 1/1996 |
| JP | 2582275 B2 | 2/1997 |
| JP | 2000-327528 A | 11/2000 |
| JP | 3242874 B2 | 1/2001 |
| JP | 2001-55307 A | 2/2001 |
| JP | 2005-314372 A | 11/2005 |
| JP | 2008-115358 A | 5/2008 |
| JP | 4341871 B2 | 10/2009 |

OTHER PUBLICATIONS

Sakuta, "Development of New Thickening Agent for Silicone Fluids", J. Soc. Cosmet. Chem. Japan, vol. 27, No. 3, 1993, pp. 480-483.

* cited by examiner

*Primary Examiner* — Blessing Fubara
*Assistant Examiner* — Jennifer Berrios
(74) *Attorney, Agent, or Firm* — Birch, Stewart, Kolasch & Birch, LLP

(57) ABSTRACT

Present invention provides a composition for a cosmetic comprising a fluorine-containing silicone polymer having a three-dimensional, cross-linked structure, prepared by addition polymerizing the following (A), (B) and (C) and containing 10 to 30 mass % of the fluorine atoms, relative to a total mass of (A) to (C), (A) a vinyl group-containing organopolysiloxane represented by the following formula (1):

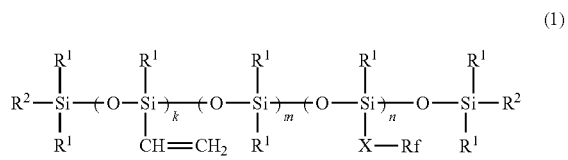

(B) an organohydrogenpolysiloxane represented by the following formula (2):

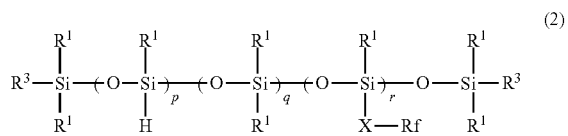

and
(C) an organopolysiloxane having a reactive group on one end alone and represented by the following formula (3),

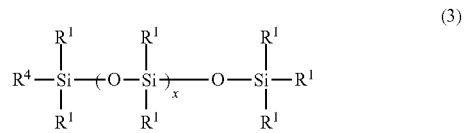

and further comprising
(D) a low viscosity silicone oil with a dynamic viscosity of 50 mm²/s or less at 25 degrees C.

4 Claims, No Drawings

COMPOSITION FOR A COSMETIC AND A COSMETIC COMPRISING THE SAME

CROSS REFERENCE

This application claims the benefits of Japanese Patent Application No. 2010-049644 filed on Mar. 5, 2010, the contents of which are herein incorporated by reference.

FIELD OF THE INVENTION

The present invention relates to a composition for a cosmetic which has good affinity with other cosmetic materials and provides a significantly light and smooth feel, more specifically, a composition for a cosmetic comprising a silicone polymer which has swellablility with low-viscosity silicone oil, and a cosmetic comprising the same.

BACKGROUND OF THE INVENTION

Silicone oil has good properties such as refreshed feel, smooth spreading and good water repellency, and therefore it has been widely used as an oil agent for cosmetics. In particular, low-viscosity silicone oil provides a cosmetic which has non-tackiness and light feel, and therefore it has been much used.

The silicone oil lacks in compatibility with general oil agents and thickening agents, and therefore, it is difficult to control a viscosity of the low-viscosity silicone oil. Oil agents such as silicone oil are made pasty with a specific silicone gel and have been commercially available as a material for adjusting membrane feel. For example, KSG-15, KSG-16 and KSG-045Z are commercially available from Shin-Etsu Chemical Co., Ltd. These materials have been widely used in various kinds of cosmetic because they can control a viscosity of cosmetics and provide a special continuous membrane feel which is not obtained from a powder material.

However, if these materials are added to cosmetics in a large amount to attain sufficient membrane feel of cosmetics, they are liable to give a somewhat tackiness to a skin treated with the cosmetics. Therefore, there is a need for a material which has lower tackiness. Japanese Patent Publication No. Hei-6-55897, Japanese Patent Publication No. Hei-8-6035, Japanese Patent No. 2582275 and Japanese Patent No. 3242874 disclose methods where a silicone polymer and low-viscosity silicone oil are processed with by a shearing force in the presence of a specific silicone gel as a thickening agent for the low-viscosity silicone oil to provide a uniform pasty composition. However, if an amount of the silicone gel added is large, the cosmetic is liable to give tackiness to a skin. According to the research in respect to a production method of a thickening agent for silicone and the thickening effect described in J. Soc. Cosmet. Chem. Jpn., 27 (3), 480-483 (1993), it is known that the presence of a silicon oil which is unreactive with a silicone polymer in the production process of the silicone polymer significantly increases the thickening effect in proportion to the amount of the silicone oil added. However, if the amount of the silicone oil added is increased, the tackiness increases also on the skin which the silicon polymer obtained is applied to.

A silicone polymer which has a side chain in a part of the crosslinking structure is suggested for improving the tackiness in Japanese Patent Application Laid-Open No. 2008-115358, but the improvement is insufficient. Further, a cosmetic with such a silicone polymer shows significantly poor oil repellency, its membrane strength is reduced by a sebum, and a function for preventing color migration is insufficient. Further, its rub resistance is insufficient. Japanese Patent Application Laid-Open No. 2000-327528 describes a method where a fluorine-containing compound, in particular a high molecular weight compound having a molecular weight of 5,000 to 1,000,000 is added to a cosmetic together with the aforesaid pasty silicone composition. However, this fluorine-containing compound with a high molecular weight have very low affinity with other materials and, therefore, is liable to separate in a cosmetic with time, increases the viscosity of the cosmetic. Accordingly, its amount and selection of the other materials are restricted.

Japanese Patent No. 4341871 describes a uniform pasty composition which has swellability with fluorine-modified silicone oils having a high content of fluorine-substituted alkyl groups, such as penta-3,3,3-trifluoropropyl pentamethyl cyclopentasiloxane, and has good water- and oil-repellency. This composition gives refreshed feel to a cosmetic, but has poor affinity with silicone materials without a fluorine-substituted alkyl group and other cosmetic low materials, and its stability is bad with time. Accordingly, its amount and selection of the other materials are restricted.

PRIOR LITERATURES

Patent Literature

[Patent Literature 1] Japanese Patent Publication No. Hei-6-55897
[Patent Literature 2] Japanese Patent Publication No. Hei-8-6035
[Patent Literature 3] Japanese Patent No. 2582275
[Patent Literature 4] Japanese Patent No. 3242874
[Patent Literature 5] Japanese Patent No. 4341871
[Patent Literature 6] Japanese Patent Application Laid-Open No. 2000-327528
[Patent Literature 7] Japanese Patent Application Laid-Open No. 2008-115358

Non Patent Literature

Non Patent Literature 1

J. Soc. Cosmet. Chem. Jpn., 27(3), 480-483 (1993)

SUMMARY OF THE INVENTION

Problems to be Solved by the Invention

It is known to add, instead of the aforesaid silicone gel, a silicone rubber powder or a powder such as a hydrophobic silica which absorbs low-viscosity silicone oil to a cosmetic to control a viscosity and a membrane feel of the cosmetic. However, these powders sometimes give undesired a powdery feel such as abrading feel and twisting feel to the cosmetic. Therefore, there is a need for a silicone gel material which does not give undesired powdery feel to the cosmetic and has lower tackiness.

An object of the present invention is to provide a composition for a cosmetic which has swellability with low-viscosity silicone oil and good affinity with other cosmetic oil agents, and to provide a cosmetic comprising the same.

Means to Solve the Problems

The present inventors have made research to solve the afore-mentioned problems and found that a fluorine-containing silicone polymer having the specific structure has excellent swellability with low-viscosity silicone oil, provides a uniform composition for a cosmetic, and provides a good cosmetic which has good storage stability, water- and oil-repellency, and lower tackiness.

The present invention provides a composition for a cosmetic comprising a fluorine-containing silicone polymer having a three-dimensional, cross-linked structure, prepared by addition polymerizing the following (A), (B) and (C) and containing 10 to 30 mass % of the fluorine atoms, relative to a total mass of (A) to (C), (A) a vinyl group-containing organopolysiloxane represented by the following formula (1):

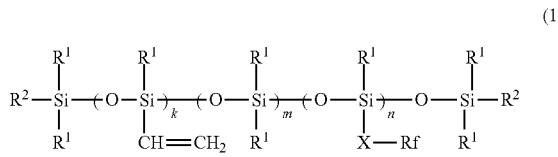

wherein Rf is a perfluoroalkyl group having 1 to 10 carbon atoms or a perfluoropolyether group having 3 to 30 carbon atoms; $R^1$ is, independently of each other, a monovalent hydrocarbon group having 1 to 10 carbon atoms without any aliphatic unsaturated bond; $R^2$ is, independently of each other, a vinyl group or a monovalent hydrocarbon group having 1 to 10 carbon atoms without any aliphatic unsaturated bond; k is an integer of 0 to 10, provided that the organopolysiloxane has at least two, per molecule, vinyl groups bonded to silicon atoms; X is a divalent organic group, m is an integer of 0 to 200, and n is an integer of 0 to 100, (B) an organohydrogenpolysiloxane represented by the following formula (2):

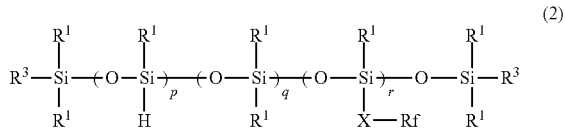

wherein $R^3$ is, independently of each other, a hydrogen atom or a monovalent hydrocarbon group having 1 to 10 carbon atoms without any aliphatic unsaturated bond; p is an integer of 0 to 10, provided that the organopolysiloxane has at least two, per molecule, hydrogen atoms bonded to silicon atoms; q is an integer of 0 to 200; r is an integer of 0 to 100, provided that n in formula (1) and r in formula (2) are not simultaneously zero; and at least either one of the number of the vinyl groups bonded to silicon atoms in formula (1) or the number of the hydrogen atoms bonded to silicon atoms in formula (2) is at least three; and Rf, X, and $R^1$ are as defined above, and (C) an organopolysiloxane having a reactive group on one end alone and represented by the following formula (3),

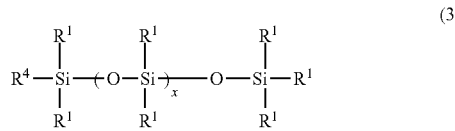

wherein $R^4$ is a hydrogen atom or a vinyl group, x is an integer of 0 to 100, and $R^1$ is as defined above, and further comprising (D) a low viscosity silicone oil with a dynamic viscosity of 50 mm²/s or less at 25 degrees C.

The present invention also provides a cosmetic comprising the same, and a cosmetic further comprising a branched silicone activator having a specific structure.

Effects of the Invention

The present composition for a cosmetic provides a cosmetic which has good affinity with other cosmetic materials and a very light and smooth feel by containing a silicone polymer which has swellability with low-viscosity silicone oil.

BEST MODES OF THE INVENTION

Fluorine-Containing Silicone Polymer

The fluorine-containing silicone polymer of the present invention is a polymeric product having a three-dimensional, cross-linked structure obtained by addition polymerizing the following organopolysiloxane components, (A), (B) and (C), and is characterized by having the particular amounts, per molecule, of fluorine atoms and silicone side chains.

Components (A) and (B) may or may not comprise a siloxane unit represented by Rf in the aforementioned formulas (1) and (2). The present fluorine-containing silicone polymer comprises 10 to 30 mass %, preferably 15 mass % to 27 mass %, of fluorine atoms, relative to a total mass of components (A) to (C). If the fluorine content is lower than the aforementioned lower limit, the effects by the modification by fluorine-containing substituents are less, so that the light feeling and smoothness characteristic to the fluorine-containing compounds are less. If the fluorine content is higher than the aforementioned upper limit, their affinity with the low viscosity silicone oil (D) is lower and, therefore, the low viscosity silicone oil is less occluded in the three-dimensional, cross-linked structure formed by the addition polymerization and tends to separate.

The each component will be described below in detail.

(A) Vinyl Group-Containing Organopolysiloxane

Component (A) represented by the following formula (1) is an organopolysiloxane which has at least two, per molecule, vinyl groups bonded to silicon atoms.

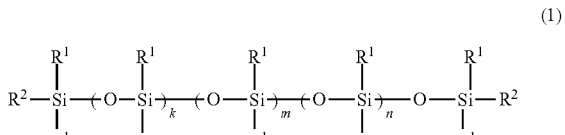

In the aforementioned formula (1), Rf is a perfluoroalkyl group having 1 to 10, preferably 3 to 6, carbon atoms or a perfluoropolyether group having 3 to 30, preferably 8 to 20, carbon atoms. Examples of the perfluoroalkyl groups include trifluoropropyl, nonafluorobutyl, tridecafluorohexyl, and heptadecafluorooctyl groups. Nonafluorobutyl and tridecafluorohexyl groups are preferred. Examples of the perfluoropolyether groups include those represented by the following formulas (4) and (5). In particular, the perfluoropolyether represented by formula (4) is preferred.

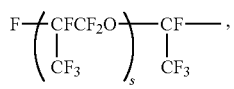  (4)

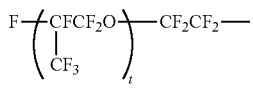  (5)

wherein s and t are each an integer of 1 to 9, preferably 2 to 5.

In the aforementioned formula (1), k is an integer of 0 to 10, m is an integer of 0 to 200, and n is an integer of 0 to 100. Preferably, k is an integer of 1 to 5, m is an integer of 50 to 120 and n is an integer of 5 to 30.

In the aforementioned formula (1), X is a divalent organic group, in particular, that having 2 to 12, preferably 2 to 8, carbon atoms and, optionally, may contain an oxygen and a nitrogen atom. Specific examples of X include the following.

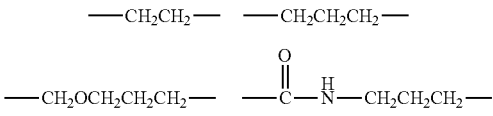

In the aforementioned formula (1), $R^1$ is, independently of each other, a monovalent hydrocarbon group having 1 to 10, preferably 1 to 4, carbon atoms without any aliphatic unsaturated bond. Examples of the monovalent hydrocarbon groups include lower alkyl groups, such as methyl, ethyl, propyl and butyl groups, cycloalkyl groups such as a cyclohexyl group, aryl groups such as phenyl, tolyl and xylyl groups and aralkyl groups such as a benzyl group. Methyl and n-butyl groups are preferred.

$R^2$ is, independently of each other, a vinyl group or a monovalent hydrocarbon group having 1 to 10, preferably 1 to 4, carbon atoms without any aliphatic unsaturated bond. Examples of the monovalent hydrocarbon groups include lower alkyl groups, such as methyl, ethyl, propyl and butyl groups, cycloalkyl groups such as a cyclohexyl group, aryl groups such as phenyl, tolyl and xylyl groups and aralkyl groups such as a benzyl group. $R^2$ is preferably a vinyl group. When k is 0, both of the $R^2$'s are a vinyl group. When k is 1, at least one of $R^2$'s is a vinyl group.

(B) Organohydrogenpolysiloxane

Component (B) is represented by the following formula (2) and has at least two hydrogen atoms, per molecule, bonded to silicon atoms so as to addition polymerize with component (A) to form a cross-linked structure.

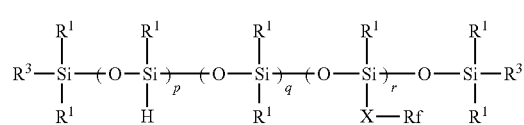  (2)

In the aforementioned formula (2), p is an integer of 0 to 10, q is an integer of 0 to 200 and r is an integer of 0 to 100. Preferably, p is an integer of 2 to 5, q is an integer of 1 to 50 and r is an integer of 0 to 20. It should be noted that n in the aforementioned formula (1) and r in the aforementioned formula (2) are not simultaneously zero. $R^3$ is, independently of each other, a hydrogen atom or a monovalent hydrocarbon group having 1 to 10, preferably 1 to 4, carbon atoms without any aliphatic unsaturated bond, and is preferably a methyl group. When p is 0, both of $R^3$'s are a hydrogen atom. When p is 1, at least one of $R^3$'s is a hydrogen atom. At least either one of the number of vinyl groups bonded to silicon atoms in formula (1) or the number of hydrogen atoms bonded to silicon atoms in formula (2) is at least three. $R^1$, X and Rf are as defined above.

(C) Organopolysiloxane Having a Reactive Group on One End Alone

Component (C) is an organopolysiloxane which bonds to component (A) and/or component (B) to form a silicone side chain. The silicone side chain in the fluorine-containing silicone polymer improves swellability of the silicone polymer with low viscosity silicone oils, and thus improves a thickening property and, consequently increases stability of the composition for a cosmetic. Component (C) of the present invention is represented by the following formula (3) and is an organopolysiloxane having a reactive group on one end alone, wherein the reactive group is either a hydrogen atom or a vinyl group bonded to a silicone atom.

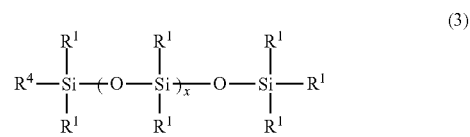  (3)

wherein $R^4$ is a hydrogen atom or a vinyl group. $R^1$ is, independently of each other, a monovalent hydrocarbon group having 1 to 10, preferably 1 to 4, carbon atoms without any aliphatic unsaturated bond. Examples of the monovalent hydrocarbon groups include lower alkyl groups, such as methyl, ethyl, propyl and butyl groups, cycloalkyl groups such as a cyclohexyl group, aryl groups such as phenyl, tolyl and xylyl groups and aralkyl groups such as a benzyl group. Methyl and n-butyl groups are preferred. X is an integer of 0 to 100, preferably 5 to 30.

The silicone side chain is introduced preferably into one out of component (A) or component (B), which has a higher content of fluorine atoms, whereby the silicone polymer is insoluble in the low viscosity silicone oil (D), but sufficiently swellable therewith to give a composition for a cosmetic which well occludes the low viscosity silicone oil (D) therein. When introducing the silicone side chain into component (A), component (C) where $R^4$ in the aforementioned formula (3) is a hydrogen atom is used in such an amount that the SiH group in component (C) is 0.1 to 0.4 mole, preferably 0.15 to 0.3 mole, per mole of the vinyl group in component (A). When introducing the silicone side chain into component (B), component (C) where $R^4$ in the aforementioned formula (3) is a vinyl group is used in such an amount that the vinyl group in component (C) is 0.1 to 0.4 mole, preferably 0.15 to 0.3 mole, per mol of the SiH group in component (B). If the amount of the reactive group in component (C) is lower than the aforementioned lower limit, the swellability of the silicone polymer with low viscosity silicone oils is bad and storage stability of the composition for a cosmetic is low. If the amount of the reactive group is higher than the aforementioned upper limit, only an insufficient amount of the reactive group remains in component (A) or (B) after introducing the silicone side chain and, accordingly, the three-dimensional, cross-linked structure is only poorly built up. Therefore, the low viscosity silicone oil is less occluded in the three-dimensional, cross-linked structure. Accordingly, when the low viscosity silicone oil (D) is used in a relatively large amount or when the composition for a cosmetic is used together with the low viscosity silicone oil (D) in processing the composition for a cosmetic by a shearing force, the composition for a cosmetic dissolves easily in the low viscosity silicone oil (D) and, therefore, the siloxane composition obtained cannot be sufficiently viscous, which is undesired.

Components (A) and (B) are reacted after the silicone side chain is introduced in (A) and/or (B), in such amounts that the SiH group in component (B) is 0.7 to 1.3 moles, preferably 0.8 to 1.1 moles, per mole of the vinyl group in component (A), whereby, the three-dimensional, cross-linked structure is formed as desired. Component (A) and component (B) preferably have the vinyl group or SiH group in the amount of 0.5 to 50 mole %. If the amount of the reactive group exceeds the aforementioned upper limit, density of the three-dimensional, cross-linked structure in the polymeric product is so high that it is difficult to occlude the low viscosity silicone oil (D) in the three-dimensional, cross-linked structure and, therefore, the low viscosity silicone oil bleeds out easily and the stability is low, which is undesired.

Composition for a Cosmetic

The addition polymerization of components (A), (B) and (C) may be carried out in the presence of the low viscosity silicone oil (D) described below. The present composition for a cosmetic comprises the silicone polymer obtained by addition polymerizing components (A), (B) and (C) and the low viscosity silicone oil (D). Another low viscosity silicone oil (D) different from the low viscosity silicone oil (D) present in the reaction may be added after the addition polymerization.

(D) Low Viscosity Silicone Oil

Component (D) is a low viscosity silicone oil having a dynamic viscosity at 25 degrees C. of 50 mm$^2$/s or less, preferably 50 mm$^2$/s to 0.65 mm$^2$/s, more preferably 10 mm$^2$/s to 0.65 mm$^2$/s. If the dynamic viscosity exceeds 50 mm$^2$/s, the silicone oil tends to bleeds out to make the composition unstable, and greasy touch appears and fresh feeling is lost, which is undesired. The low viscosity silicone oil is an organopolysiloxane having no functionality, that is, having no alkenyl group or SiH group which is bonded to a silicone atom and capable of participating in hydrosilylation. Examples of the low viscosity silicone oil include liner or branched methyl polysiloxane, methyl phenyl polysiloxane, ethyl polysiloxane, ethyl methyl polysiloxane and ethyl phenyl polysiloxane which all have a low polymerization degree, cyclic octamethylcyclotetrasiloxane and decamethylcyclopentasiloxane. One or more of these are properly selected, as required.

Component (D) is used suitably in an amount of 10 to 1000 parts by mass, preferably 20 to 700 parts by mass, more preferably 50 to 500 parts by mass, relative to 100 parts by mass of a total of components (A) to (C). If the amount of the low viscosity silicone oil is less than 10 parts by mass, the effects of the low viscosity silicone oil are so less that thickening property of the resulting composition is low; when the composition is blended with rubber or plastics, the effect of providing flexibility or a lubricating property is less, which is undesired; and further, the transparency of the composition obtained tends to be lost. If the amount of the low viscosity silicone oil (D) is larger than 1000 parts by mass, the reaction among components (A), (B) and (C) is less and, therefore, a composition does not have a sufficient thickening property. Preferably, 10 to 200 parts by mass, in particular 20 to 100 parts by mass, of component (D) is used in the addition reaction with 100 parts by mass of a total of components (A) to (C), whereby the reaction product gradually changes its form from a liquid, via a soft mass, to powder, as the polymerization proceeds.

The addition polymerization of components (A), (B) and (C) in the presence of the low viscosity silicone oil (D) may be carried out in any conventional method, for instance, at room temperature or under heating to approximately 50 to 150 degrees C. in the presence of an organic solvents-soluble platinum compound, such as chloroplatinic acid, alcohol-modified chloroplatinic acid or a complex of chloroplatinic acid with vinylsiloxane, or an organic rhodium compound. As the organic solvent, use may be made of aliphatic alcohols, such as methanol, ethanol, 2-propanol and butanol, aromatic hydrocarbons, such as benzene, toluene and xylene, aliphatic or alicyclic hydrocarbons, such as n-pentane, n-hexane and cyclohexane, and halogenated hydrocarbons, such as dichloromethane, chloroform, tetrachloromethane, trichloroethane, trichloroethylene and fluorinated and chlorinated hydrocarbons.

Examples of the catalyst preferably include chloroplatinic acid and platinum compounds, such as Pt(PPh$_3$)$_3$, which are used in hydrosilylation described in U.S. Pat. Nos. 3,159,601, 3,159,662 and 3,775,452. The platinum compounds are preferably complexes with, for instance, vinyl siloxane or those modified with alcohol. Inter alia, preferred is chloroplatinic acid or the complex of chloroplatinic acid with vinyl siloxane which are described in Japanese Patent Publication No. Sho-33-9969.

In an exemplary method for the addition polymerization, components (A), (B), (C) and (D) are blended in desired amounts in a reactor such as a planetary mixer equipped with a stirring equipment, and a catalyst is added, followed by stirring at an appropriate temperature, for instance, approximately 50 to 150 degrees C. Here, it is preferred that either component (A) or (B) which has a higher fluorine content is addition reacted with component (C) to introduce the silicone side chain into the organopolysiloxane chain of this (A) or (B) and, then, this organopolysiloxane is addition polymerized with the other organopolysiloxane. Such a two-step process does not lower the compatibility among components (A) to (C) and, therefore, the addition polymerization proceeds smoothly. If components (A) and (B) are addition polymerized first, the reactivity for forming the silicone side chains is very low. If components (A) to (C) are fed at once and reacted simultaneously, cross-links are formed before a desired amount of the silicone side chains is introduced into the main chain, i.e., organopolysiloxane backbone, and, therefore, the less amount of the silicone side chains is introduced, whereby the characteristics of the silicone side chains tend not to be sufficiently exerted.

The present composition changes its form from a liquid, via a soft mass, to powder as the polymerization proceeds. In order to obtain a composition in a state of fine powder, the composition obtained in a state of powder is processed by a shearing force. The powder composition is pulverized in this processing to give fine powder of the composition. This fine powder composition does not show bleed-out on the surface, is white, homogeneous in composition, smooth in touch and flexible to a proper extent.

In order to obtain a pasty composition or a greasy composition, the low viscosity silicone oil (D) may be further added to the lump or powder composition, which is then processed by a shearing force. The low viscosity silicone oil is added in such an amount that a total amount of the low viscosity silicone oil contained in the composition for a cosmetic is 10 to 1000 parts by mass, preferably 20 to 700 parts by mass, more preferably 50 to 500 parts by mass, relative to 100 parts by mass of a total of components (A) to (C). The aforementioned processing gives a kneaded and homogeneous composition for a cosmetic. If the amount of the low viscosity silicone oil is less than 10 parts by mass, the resulting composition is not in a homogeneous, pasty form. If the amount of the low viscosity silicone oil exceeds 1000 parts by mass, the end product does not acquire a sufficient thickening property and, therefore, is not in a good pasty or greasy state.

A relatively highly viscous, homogeneous and pasty composition with smooth appearance is obtained by processing the polymerization composition by a shearing force as mentioned above. If the shearing force is not applied or insufficient, the fluorine-containing silicone polymer dissolves insufficiently in the low viscosity silicone oil, so that the fluorine-containing silicone polymer and the low viscosity silicone oil do not mix with each other and provide an unhomogeneous composition, whereby the composition is low viscous and does not have a sufficient thickening property. Further, a less-swelled fluorine-containing silicone polymer remains in the end composition whose touch is, therefore, rough and the appearance is coarse. The processing by a shearing force can be carried out by a kneading means, such as a three-roll mill, a two-roll mill, a sand grinder, a colloid mill and a Gaulin homogenizer. The kneading means may be selected properly, depending on the properties and state of the material to be processed. Inter alia, processing by a three-roll mill is preferred.

This invention also provides a cosmetic comprising the aforementioned composition for a cosmetic. The present composition for a cosmetic has swellability with low-viscosity silicone oil, good affinity with other materials and lower tackiness. Therefore, the present composition for a cosmetic can provide a cosmetic which has light feel without tackiness. The content of present composition for a cosmetic in the cosmetic ranges from 0.1 to 70 mass %, preferably 1.0 to 50 mass %, relative to a total mass of the cosmetic. If the amount is less than the lower limit, the storage stability of the cosmetic tends to be lost. If the amount exceeds the upper limit, refreshed feel may not be obtained on a skin.

Branched Silicon Activator

The cosmetic of the present invention further contains the specific branched silicone activator to reduce the tacky feel associated with emulsification. The branched silicone activator is a surfactant agent which has a branch silicone moiety as a hydrophobic group and a polyoxyalkylene group or polyglycerin group as a hydrophilic group. This is known as PEG-9 polysiloxyethyl dimethicone, lauryl PEG-9 polydimethylsiloxyethyl dimethicone, polyglyceryl-3 polydimethylsiloxyethyl dimethicone, lauryl polyglyceryl-3 polydimethylsiloxyethyl dimethicone, and polyglyceryl-3 disiloxane dimethicone, and commercial products thereof can be used. Examples of the commercial products include KF-6028, KF-6028P, KF-6038, KF-6100, KF-6104, and KF-6105, all available from Shin-Etsu Chemical Co., Ltd. It is known that the activator having a polyglycerin chain is excellent in dispersing a pigment. The content of the activator in the cosmetic ranges from 0.05 to 6 mass %, preferably 0.05 to 4 mass %, relative to a total mass of the cosmetic, depending on a form of the cosmetic.

The cosmetic may contain any other components which are commonly used in cosmetics, such as oil agents, powder components, surfactants, thickening agents, film-forming agents, ultraviolet absorbing agents, and medical agents. The content of the components in the cosmetic may be such as not to adversely affect the effects of the present invention. Further, water may be contained in the cosmetic of the present invention, if needed. The content of water in the cosmetic ranges from 0.1 to 90 mass % relative to a total mass of the cosmetic, and may be increased or decreased, depending on a form of the cosmetic. The cosmetic comprising water can be an aqueous solution, an oil-in-water emulsion (O/W type), a water-in-oil emulsion (W/O type), an O/W/O type emulsion, and a W/O/W type emulsion.

(a) Oil Agent

The oil agent is not limited to any particular one, and any oil agent which is commonly used in cosmetics, such as ones liquid, semisolid or solid at room temperature. Examples of the oil agent include hydrocarbon oils, higher fatty acids, higher alcohols, ester oils, natural animal or plant oils, fluorized oils and silicone oils. In this specification, room temperature means 25 degrees C., give or take 5 degrees C. The content of the oil agent (a) in the cosmetic may be such as not to adversely affect the effects of the present invention, and ranges preferably from 0.1 to 50 mass %, more preferably 1 to 30 mass %, relative to a total mass of the cosmetic, depending on a form of the cosmetic. If the amount is less than the lower limit, the effects such as smoothness and moisture-retaining property by the oil may not be attained. If the amount exceeds the upper limit, the storage stability tends to be lost.

Examples of the hydrocarbon oils include ozokerite, α-olefin oligomers, paraffin, isoparaffin, isododecane, squalane, ceresin, paraffin wax, polyethylene wax, polyisobutylene, hydrogenated polyisobutene, microcrystalline wax, and Vaseline. Among these, the oil which is volatile at room temperature remains a membrane on a skin after volatilized to provide refreshed feel. The liquid oil which is non-volatile is used to improve touch and gloss, and the solid oil is used to increase a viscosity of the other oil agent or solidify the same.

The higher fatty acids may be linear or branched, saturated or unsaturated. Examples of the higher fatty acids include lauric acid, myristic acid, palmitic acid, stearic acid, behenic acid, oleic acid, isostearic acid, and 12-hydroxystearic acid. These are used as an emulsifying agent, an emulsifying adjuvant, and a thickener for oil or to stabilize the cosmetic. In particular, isostearic acid which is a branched fatty acid is useful as an emulsifying adjuvant.

Examples of the higher alcohols include myristyl alcohol, palmityl alcohol, stearyl alcohol, behenyl alcohol, oleyl alcohol, isostearyl alcohol, hexyldodecanol, octyl dodecanol, cetyl alcohol, cholesterol, phytosterol, batyl alcohol, and cerakyl alcohol. These are useful as an emulsifying adjuvant.

Examples of the ester oils include monoesters such as cetyl 2-ethylhexanoate, isononyl isononanate, isotridecyl isononanate, 2-ethylhexyl palmitate, octyldodecyl myristate, neopentylglycol dioctanoate and neopentylglycol dicaprate; diacid esters such as diisopropyl sebacate and diisostearyl malate; triglycerides such as triethyl hexanoine; polyglyceryl esters such as polyglyceryl-2 triisostearate; trimethylolpropane derivatives such as trimethylolpropane triisostearate and trimethylolpropane tri-2-ethylhexanoate; phytosterol esters such as phytosteryl 12-hydroxystearate and phytosteryl isostearate; amino acid esters such as 2-octyldodecyl N-lauroyl-L-glutamate; hydroxystearates such as dipentaerythritol hydroxystearate, stearate or rosinate; and pentaerythritol esters of fatty acids such as rosinate. They provide the effects of adjusting feeling, compatibilizing the components, and improving dispersibility of a pigment, gloss, emollient and moisturizing property.

Examples of the animal or plant oils include ones which are obtained by purifying avocado oil, flaxseed oil, almond oil, olive oil, Ibota wax, cacao butter, carnauba wax, candelilla wax, wheat germ oil, sesame oil, rice germ oil, rice bran oil, safflower oil, shear butter, jojoba oil, squalane oil, soybean oil, camellia oil, evening primrose oil, corn oil, rapeseed oil, rice bran wax, palm kernel oil, castor oil, sunflower oil, macadamia nut oil, beeswax, meadowfoam oil, cottonseed oil, japanese wax, montan wax, earthnut oil, lanolin, liquid lanolin and egg-yolk oil; and hydrogenated ones thereof such as hydrogenated jojoba wax, hydrogenated castor oil, hydrogenated rapeseed oil and reduced lanolin.

Examples of the fluorinated oil include perfluoropolyoxyalkylene, perfluorodecaline and perfluorooctane.

Examples of the silicone oils include linear silicone oils such as dimethylpolysiloxane, caprylyl methicone, cetyl dimethicone, phenyl trimethicone, diphenyl siloxy phenyl trimethicone, methylphenylpolysiloxane and methylhexylpolysiloxane; cyclic organopolysiloxanes such as octamethylcyclotetrasiloxane, decamethylcyclopentasiloxane, dodecamethylcyclohexasiloxane and tetramethyltetraphenylcyclotetrasiloxane; branched organopolysiloxanes such as tristrimethylsiloxymethylsilane and tetrakistrimethylsiloxysilane; silicone rubbers such as high-polymerized dimethylpolysiloxane rubber, amino-modified organopolysiloxane rubber and dimethylsiloxane-methylphenylsiloxane-copolymer rubber; higher fatty acid-modified organopolysiloxane; alkyl-modified organopolysiloxane; long-chain alkyl-modified organopolysiloxane; amino-modified organopolysiloxane and fluorized organopolysiloxane. Among these, preferred are ester oils having a branched structure such as triethylhexanoin, neopentylglycol diethylhexanoate and isotridecyl isononanoate, and silicone oils which have a kinetic viscosity at room temperature of 1.5 to 10 $mm^2/s$, because they have lower tackiness and refreshed feel.

(b) Powder Component

As the powder component, any powder which is commonly used in cosmetics may be used, regardless of a shape such as spherical, acicular, plate-like, dendritic, fibrous and amorphous; a size, and particle structure such as porous, nonporous, hollow and hollow porous. Examples of the powder include inorganic powder, organic powder, metal soaps and coloring pigments. These powders may be treated with a metal soap, silica, aluminum oxide, aluminum hydroxide and by any other conventional method, and may be a complex powder, in order to reduce the surface activity, increase the dispersibility and improve the touch when the cosmetic is applied. The content of the powder in the cosmetic may be such as not to adversely affect the effects of the present invention, and ranges from 0.1 to 99 mass %, preferably 0.1 to 50 mass %, more preferably 0.5 to 40 mass %, relative to a total mass of the cosmetic, depending on the form of the cosmetic.

Examples of the inorganic powder include ultraviolet-absorbing and scattering agents such as particulate titanium oxide, particulate zinc oxide and particulate cerium oxide; and extender pigments such as barium sulfate, calcium carbonate, magnesium carbonate, talc, mica, kaolin, sericite, synthetic bronze mica, silica, hydroxyapatite and boron nitride. The ultraviolet-absorbing and scattering agents may be dispersed in oil in advance. Examples of the commercial products thereof include SPD-T5 and SPD-Z5, all available from Shin-Etsu Chemical Co., Ltd.

Examples of the organic powder include polyester powder, polyethylene powder, polystyrene powder, polyurethane powder, polymethylmethacrylate powder, methyl methacrylate crosspolymer, cellulose powder, silk powder, nylon powder such as Nylon 12 and Nylon 6, fibrous powder thereof, crosslinked silicone fine powder having crosslinked structure from dimethylpolysiloxane, crosslinked polymethylsylsesquioxane spherical fine powder, fine powder which is obtained by coating a surface of crosslinked organopolysilicone elastomer with polymethylsylsesquioxane particles, laminated powder of a resin, starch powder, fatty acid starch derivatives powder, and lauroyl lysine.

In Particular, the powder which is obtained by coating a surface of a crosslinked organopolysilicone spherical elastomer such as (vinyldimethicone/methiconesylsesquioxane) crosspolymer and (diphenyldimethicone/vinyldiphenyldimethicone/sylsesquioxane) crosspolymer with polymethylsylsesquioxane particles may be uses as a part of the powder component, to thereby attain good dispersibility and to yield refreshed and soft feel to the cosmetic. Examples of the commercial product thereof include KSP-100, KSP-101, KSP-102, KSP-105 and KSP-300, all available from Shin-Etsu Chemical Co., Ltd.

Examples of the metal soap, i.e., metal salt of surfactant, include zinc stearate and aluminum stearate.

Examples of the coloring pigment include inorganic coloring pigments such as titanium oxide, iron oxide, titanium black, carbon black, chromium hydroxide, chromium oxide, iron blue, ultramarine blue and aluminum powder; tar colors such as Red No. 226 and Yellow No. 4; natural pigments such as carmine; pearl pigments such as titanium mica, titanium mica coated with iron oxide and synthetic bronze mica coated with titanium oxide.

These powders may be surface treated with one or more commercial film-forming agents or surface treatment agents in an amount not to adversely affect the present effects. Examples of the surface treatment agent include KF-9908, KF-9909 and KP-574, all available from Shin-Etsu Chemical Co., Ltd. They have excellent dispersivility, as desired.

(c) Surfactant

The surfactant is not limited to any particular one, and may be one which is commonly used in cosmetics. Examples of the surfactant include anionic, cationic, nonionic or amphoteric surfactants. The content of the surfactant in the cosmetic may be such as not to adversely affect the effects of the present invention, and ranges from 0.1 to 20 mass %, preferably 0.1 to 10 mass %, relative to a total mass of the cosmetic.

An example of the anionic surfactant is fatty acid soap such as sodium stearate which is known as an O/W type emulsifier. Branched fatty acid soaps such as sodium isostearate may be used to increase stability of a W/O type emulsion. Examples of the amphoteric surfactant include betaine, phosphatidylcholine, aminocarboxylate salts, imidazoline derivatives, and amide amine type surfactants.

Examples of the nonionic surfactant include sorbitan fatty acid esters, glycerin fatty acid esters, polyglycerin fatty acid esters, propylene glycol fatty acid esters, sucrose fatty acid esters, methyl glucoside fatty acid esters, alkyl polyglucoside, polyoxyalkylene fatty acid esters, polyoxyethylene hydrogenated castor oil, surfactants whose hydrophobic group is hydrocarbon and silicone surfactants other than the present silicone compound.

(d) Thickening Agent

The thickening agent is not limited to any particular one, and may be any one which is commonly used in cosmetics. The thickening agent is classified in an aqueous type and oily type. The content of the thickening agent in the cosmetic may be such as not to adversely affect the effects of the present invention, and ranges from 0.1 to 30 mass %, preferably 0.1 to 10 mass %, relative to a total mass of the cosmetic.

Examples of the aqueous type thickening agent include fine powder silica; inorganic powders such as bentonite and hectorite; gum arabic, guar gum, carrageenan, agar, quince seed, locust bean gum, xanthane gum, pullulan, sodium carboxymethylcellulose, hydroxyethyl cellulose; vinyl polymers such as carboxy vinyl polymer; and acrylic water-soluble polymers such as (ammonium acryloyldimethyl taurate/VP) copolymer, (sodium acrylate/sodium acryloyldimethyl taurate) copolymer, (hydroxyethyl acrylate/sodium acryloyldimethyl taurate) copolymer and polyacrylamide. The acrylic polymers can provide the stability to the O/W type emulsification with relative ease.

Examples of the oil type thickening agent include hydrophobized fine powder silica such as silylated silica; organic modified clay minerals such as disteardimonium hectorite; metal soaps such as aluminum stearate; polysaccharide fatty acid esters such as dextrin palmitate/2-ethylhexanoate and inulin stearate; sucrose fatty acid esters such as sucrose stearate acetate; and crosslinked organopolysiloxane.

A small amount of the hydrophobized fine powder silica can absorbs a large amount of oil components. The organic modified clay mineral can improve the emulsion stability in combination with the surfactant, the viscosity of the cosmetic can be increased by a polar additive such as propylene carbonate. The dextrin palmitate/2-ethylhexanoate can form a thickened gel with less syneresis. Therefore, these are useful for thickening and stabilizing the oily or W/O type cosmetic.

The crosslinked organopolysiloxane swells with a liquid oil, containing a larger weight of the liquid oil than its own weight, and may or may not contain a hydrophilic group in the molecule. Examples of commercial products thereof include KSG series, available from Shin-Etsu Chemical Co., Ltd., which is made pasty with oil. These crosslinked organopolysiloxanes can be used together with the present composition for a cosmetic.

(e) Film-Forming Agent

The film-forming agent is not limited to any particular one, and may be one which is commonly used in cosmetics. Examples of the film-forming agent include aqueous type ones and oily type ones. Examples of the aqueous type film-forming agent include polyvinyl alcohol, polyvinyl pyrrolidone, vinyl acetate/vinyl pyrrolidone copolymers and emulsions of acrylic acid copolymers. The content of the film-forming agent in the cosmetic may be such as not to adversely affect the effects of the present invention, and ranges from 0.1 to 30 mass %, preferably 0.5 to 20 mass %, relative to a total mass of the cosmetic.

Examples of the oily type film-forming agent include α-olefin/vinyl pyrrolidone copolymers such as eicosene/vinyl pyrrolidone copolymer; acrylic acid/alkylacrylate copolymer; silicone network resins such as trimethylsiloxy silicate; and acryl/silicone graft or block copolymers such as (alkylacrylate/dimethicone) polymer. The acrylsilicone resin and the silicone network resin may contain a pyrolidone moiety, long-chain alkyl moiety, polyoxyalkylene moiety, fluoroalkyl moiety and anion moiety such as carboxylic acid in the molecule. Examples of the commercial products thereof include KP-543, KP-545, KP-550, all available from Shin-Etsu Chemical Co., Ltd.

(f) Ultraviolet Absorbing Agent

The ultraviolet absorbing agent is not limited to any particular one, and may be one which is commonly used in cosmetics. Examples of the ultraviolet absorbing agent include polysilicone-15, octocrylene, ethylhexyl methoxycinnamate, tert-butyl methoxydibenzoylmethane, methylene bis-benzotriazolyl tetramethylbutylphenol, octyl salicylate, homosalate, phenylbenzimidazole sulfonic acid, hydroxy methoxybenzophenone sulfonic acid and octyl dimethyl-PABA (2-ethylhexyl para-dimethylaminoazobenzoate).

(g) Medical Agent

Examples of the medical agent include an antiperspirant such as aluminum chlorohydrate; an antioxidant such as tocopherol; amino acids such as glycine, serine, arginine and glutamic acid, and derivatives thereof; a nicotine acid class and a vitamin class such as a vitamin A class such as vitamin A oil and retinol, a vitamin B class such as pyridoxine hydrochloride, panthenol, pantothenyl ethyl ether, nicotinic-acid amide and cyanocobalamine, a vitamin C class such as ascorbyl palmitate and ascorbyl glucoside, and a vitamin E class such as α-tocopherol, and derivatives thereof; and anti-inflammatory agent such as dipotassium glycyrrhizate.

The present composition for a cosmetic can be added to various kinds of cosmetics such as skincare cosmetics, makeup cosmetics, hair cosmetics, antiperspirants, and UV-ray protective cosmetics. The form of the cosmetic is not limited to any particular one, and may be solid, powder, liquid, and emulsion such as water-in-oil emulsion, oil-in-water emulsion and non-aqueous emulsion. More specific examples of the cosmetic include lotion, milky lotion, cream, cleansing, pack, massage product, cosmetic essence, cosmetic oil, cleaning agent, hand cream, lip balm, wrinkle-concealing cosmetic, makeup base, concealer, white powder, powder foundation, liquid foundation, cream foundation, oily foundation, blusher, eye shadow, mascara, eyeliner, eyebrow cosmetic, rouge, manicure, shampoo, rinse, conditioner, hair setting agent, antiperspirant cosmetic, sunscreen milky lotion and sunscreen cream, but not limited to these.

EXAMPLES

The present invention will be described in detail by referring to the Examples and the Comparative Examples below, but is not limited thereto.

Example 1

To a planetary mixer were added 100.0 g of the vinyl group-containing organopolysiloxane represented by the following formula (6) (fluorine content: 25.5% by mass; vinyl group content: $2.96 \times 10^{-2}$ mol/100 g):

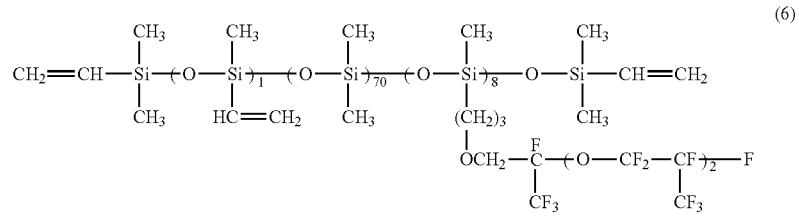

5.27 g of the organohydrogenpolysiloxane represented by the following formula (7) (SiH group content: $5.64 \times 10^{-3}$ mol/5.27 g):

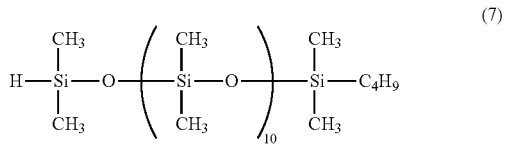
(7)

and 165.8 g of dimethylpolysiloxane having a dynamic viscosity of 2 mm²/s. 0.017 Gram of a solution of a complex of platinum with vinyl siloxane in toluene (corresponding to 0.17 mg of Pt) was added and stirred at 80 degrees C. for 1 hour.

Then, to the aforementioned reaction mixture were added 5.26 g of the organohydrogenpolysiloxane represented by the following formula (8) (fluorine content: 18.4% by mass; SiH content: $2.26 \times 10^{-2}$ mol/5.26 g):

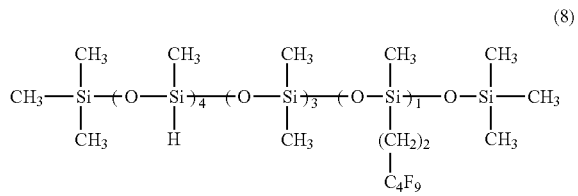
(8)

and 0.017 g of the aforementioned solution of the platinum complex and stirred at 80 degrees C. for another 1 hour to obtain a dispersion of a silicone polymer in dimethylpolysiloxane. The dispersion of the silicone polymer obtained was white and flexible powder with a fluorine content in the silicone polymer of 23.9% by mass, calculated precluding the dimethylpolysiloxane (hereinafter referred to as "silicone polymer 1").

100.0 Parts by mass of the aforementioned silicone polymer 1 and 150.0 parts by mass of dimethylpolysiloxane with a dynamic viscosity of 2 mm²/s were mixed to disperse and kneaded by a shearing force by a three-roll mill, so that the silicone polymer swelled with the dimethylpolysiloxane to give a colorless and transparent pasty composition for a cosmetic.

Example 2

To a planetary mixer were added 100.0 g of the vinyl group-containing organopolysiloxane represented by the following formula (9) (fluorine content: 20.6% by mass; vinyl group content: $3.61 \times 10^{-2}$ mol/100 g):

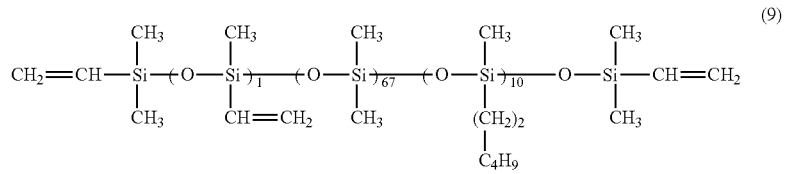
(9)

6.43 g of the organohydrogenpolysiloxane represented by the aforementioned formula (7) (SiH group content: $6.88 \times 10^{-3}$ mol/6.43 g), and 110.3 g of decamethylpentasiloxane having a dynamic viscosity of 4 mm²/s. 0.017 Gram of a solution of a complex of platinum with vinyl siloxane in toluene (corresponding to 0.17 mg of Pt) was added and stirred at 80 degrees C. for 1 hour.

Then, to the aforementioned reaction mixture were added 3.83 g of the organohydrogenpolysiloxane represented by the following formula (10) (SiH group content: $2.75 \times 10^{-2}$ mol/3.83 g):

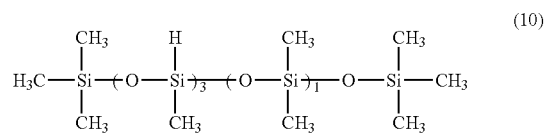
(10)

and 0.017 gram of the solution of the complex of platinum with vinyl siloxane in toluene and stirred at 80 degrees C. for another 1 hour to obtain a silicone polymer dispersion in decamethylcyclopentasiloxane. The obtained dispersion of the silicone polymer was white and flexible powder with a fluorine content in the silicone polymer of 18.7% by mass, calculated precluding the decamethylcyclopentasiloxane (hereinafter referred to as "silicone polymer 2").

100.0 Parts by mass of the aforementioned silicone polymer 2 and 200.0 parts by mass of decamethylcyclopentasiloxane were mixed to disperse and kneaded by a shearing force by a three-roll mill, so that the silicone polymer swelled with the decamethylcyclopentasiloxane to give a colorless and transparent pasty composition for a cosmetic.

Example 3

To a planetary mixer were added 100.0 g of the organohydrogenpolysiloxane represented by the following formula (11) (fluorine content: 24.9% by mass; SiH group content: $6.03 \times 10^{-2}$ mol/100 g):

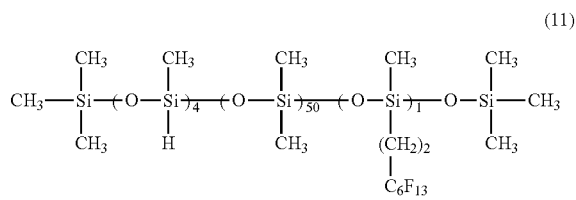
(11)

8.90 g of the organopolysiloxane represented by the following formula (12) (vinyl group content: $1.09 \times 10^{-2}$ mol/8.90 g):

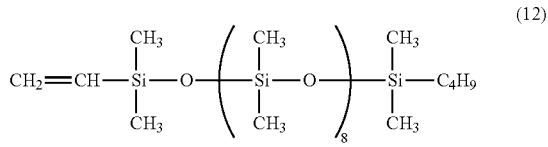

(12)

and 188.4 g of tristrimethylsiloxymethylsilane with a dynamic viscosity of 1.5 mm²/s. 0.028 Gram of a solution of a complex of platinum with vinyl siloxane in toluene (corresponding to 0.28 mg of Pt) was added and stirred at 80 degrees C. for 1 hour.

Then, to the aforementioned reaction mixture were added 79.5 g of the vinyl group-containing organopolysiloxane represented by the following formula (13) (fluorine content: 20.4% by mass; vinyl group content: $4.38 \times 10^{-2}$ mol/79.5 g):

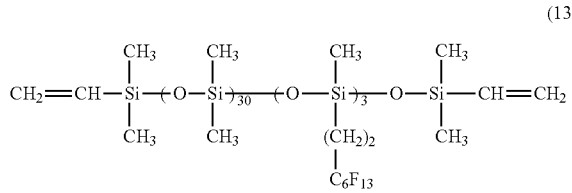

(13)

and 0.028 g of the aforementioned solution of the complex of platinum and stirred at 80 degrees C. for another 1 hour to obtain a dispersion of the silicone polymer in tristrimethylsiloxymethylsilane. The obtained dispersion of the silicone polymer was white and flexible powder with a fluorine content in the silicone polymer of 21.8% by mass, calculated precluding the tristrimethylsiloxymethylsilane (hereinafter referred to as "silicone polymer 3").

100.0 Parts by mass of the aforementioned silicone polymer 3 and 250.0 parts by mass of tristrimethylsiloxymethylsilane were mixed to disperse and kneaded by a shearing force by a three-roll mill, so that the silicone polymer swelled with the tristrimethylsiloxymethylsilane to give a colorless and transparent pasty composition for a cosmetic.

Example 4

To a planetary mixer were added 100.0 g of the vinyl group-containing organopolysiloxane represented by the following formula (14) (fluorine content: 25.9% by mass; vinyl group content: $3.25 \times 10^{-2}$ mol/100 g):

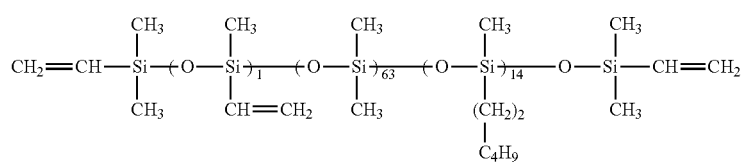

(14)

6.57 g of the organohydrogenpolysiloxane represented by the aforementioned formula (7) (SiH group content: $6.88 \times 10^{-3}$ mol/6.57 g) and 109.9 g of dimethylpolysiloxane with a dynamic viscosity of 2 mm²/s. 0.017 Gram of a solution of a complex of platinum with vinyl siloxane in toluene (corresponding to 0.17 mg of Pt) was added and stirred at 80 degrees C. for 1 hour.

Then, to the aforementioned reaction mixture was added 3.36 g of the organohydrogenpolysiloxane represented by the aforementioned formula (10) (SiH group content: $2.42 \times 10^{-2}$ mol/3.36 g) and 0.017 g of the aforementioned solution of the complex of platinum were added and stirred at 80 degrees C. for another 1 hour to obtain a dispersion of the silicone polymer in dimethylpolysiloxane. The obtained dispersion of the silicone polymer was white and flexible powder with a fluorine content in the silicone polymer of 23.6% by mass, calculated precluding the dimethylpolysiloxane (hereinafter referred to as "silicone polymer 4").

100.0 Parts by mass of the aforementioned silicone polymer 4 and 185.7 parts by mass of dimethylpolysiloxane with a dynamic viscosity of 2 mm²/s were mixed to disperse and kneaded by a shearing force by a three-roll mill, so that the silicone polymer swelled with the dimethylpolysiloxane to give a colorless and transparent pasty composition for a cosmetic.

Comparative Example 1

To a planetary mixer were added 100.0 g of the vinyl group-containing organopolysiloxane represented by the following formula (15) (fluorine content: 20.6% by mass, vinyl group content: $2.41 \times 10^{-2}$ mol/100.0 g):

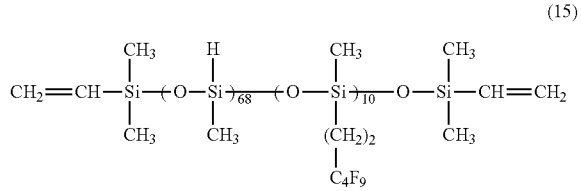

(15)

3.19 g of the organohydrogenpolysiloxane represented by the aforementioned formula (10) (SiH group content: $2.29 \times 10^{-2}$ mol/3.19 g), and 113.2 g of decamethylcyclopentasiloxane having a dynamic viscosity of 4 mm²/s. 0.034 Gram of a solution of a complex of platinum with vinyl siloxane in toluene (corresponding to 0.34 mg of Pt) was added and stirred at 80 degrees C. for another 1 hour to obtain a dispersion of the silicone polymer in decamethylcyclopentasiloxane. The obtained dispersion of the silicone polymer was white and flexible powder with a fluorine content in the silicone polymer of 20.0% by mass, calculated precluding the decamethylcyclopentasiloxane (hereinafter referred to as "silicone polymer 5").

100.0 Parts by mass of the aforementioned silicone polymer 5 and 200.0 parts by mass of decamethylcyclopentasiloxane were mixed to disperse and kneaded by a shearing force by a three-roll mill, so that the silicone polymer swelled with the decamethylcyclopentasiloxane to give a colorless and transparent pasty composition for a cosmetic.

Comparative Example 2

To a planetary mixer were added 100.0 g of the vinyl group-containing organopolysiloxane represented by the following formula (16) (fluorine content: 35.4% by mass, vinyl group content: $2.19 \times 10^{-2}$ mol/100.0 g):

(16)

$$CH_2=CH-\underset{\underset{CH_3}{|}}{\overset{\overset{CH_3}{|}}{Si}}-(O-\underset{\underset{HC=CH_2}{|}}{\overset{\overset{CH_3}{|}}{Si}})_{\overline{1}}-(O-\underset{\underset{CH_3}{|}}{\overset{\overset{CH_3}{|}}{Si}})_{\overline{63}}-(O-\underset{\underset{(CH_2)_3}{|}}{\overset{\overset{CH_3}{|}}{Si}})_{\overline{15}}-O-\underset{\underset{CH_3}{|}}{\overset{\overset{CH_3}{|}}{Si}}-CH=CH_2$$
$$OCH_2-\underset{\underset{CF_3}{|}}{\overset{\overset{F}{|}}{C}}-(O-CF_2-\underset{\underset{CF_3}{|}}{CF})_{\overline{2}}-F$$

3.90 g of the organohydrogenpolysiloxane represented by the aforementioned formula (7) (SiH group content: $4.17 \times 10^{-3}$ mol/3.90 g), and 159.3 g of dimethylpolysiloxane having a dynamic viscosity of 2 mm²/s. 0.016 Gram of a solution of a complex of platinum with vinyl siloxane in toluene (corresponding to 0.16 mg of Pt) was added and stirred at 80 degrees C. for 1 hour. Then, 2.32 g of the organohydrogenpolysiloxane represented by the aforementioned formula (10) (SiH group content: $1.67 \times 10^{-2}$ mol/2.32 g) and 0.016 g of the aforementioned solution of the complex of platinum were added and stirred at 80 degrees C. for another 1 hour to obtain a dispersion of the silicone polymer in dimethylpolysiloxane. The obtained dispersion of the silicone polymer was white and flexible powder with a fluorine content in the silicone polymer of 33.3% by mass, calculated precluding the dimethylpolysiloxane (hereinafter referred to as "silicone polymer 6").

100.0 Parts by mass of the aforementioned silicone polymer 6 and 150.0 parts by mass of dimethylpolysiloxane having a dynamic viscosity of 2 mm²/s were mixed to disperse and kneaded by a shearing force by a three-roll mill, so that the silicone polymer swelled with the dimethylpolysiloxane to give a colorless and transparent pasty composition for a cosmetic.

Comparative Example 3

A silicone composition which was obtained by kneading a dimethylpolysiloxane polymer with decamethylcyclopentasiloxane to swell (trade name: KSG-15, ex Shin-Etsu Chemical Co., Ltd.)

Comparative Example 4

To a planetary mixer were added 100.0 g of the vinyl group-containing organopolysiloxane represented by the aforementioned formula (16) (fluorine content: 35.4% by mass, vinyl group content: $2.19 \times 10^{-2}$ mol/100 g), 3.05 g of the organohydrogenpolysiloxane represented by the aforementioned formula (10) (SiH group content: $2.19 \times 10^{-2}$ mol/3.05 g), and 102.9 g of dimethylpolysiloxane having a dynamic viscosity of 2 mm²/s. 0.012 Gram of a solution of a complex of platinum (corresponding to 0.12 mg of Pt) was added and stirred at 80 degrees C. for another 1 hour to obtain a dispersion of the silicone polymer in dimethylpolysiloxane. The obtained dispersion of the silicone polymer was white and flexible powder with a fluorine content in the silicone polymer of 34.4% by mass, calculated precluding the dimethylpolysiloxane (hereinafter referred to as "silicone polymer 7").

100.0 Parts by mass of silicone polymer 7 and 150.0 parts by mass of dimethylpolysiloxane having a dynamic viscosity of 2 mm²/s were mixed to disperse and kneaded by a shearing force by a three-roll mill, but the silicone polymer did not swell and remained in such a state that powder was dispersed in dimethylpolysiloxane. Accordingly, this composition was not subjected to the following evaluation.

Examples 1 to 4 and Comparative Example 1 to 3

The compositions for a cosmetic of Examples 1 to 4 and Comparative Examples 1 to 3 were evaluated on the following properties. The results are as shown in Table 1.

[Water- and Oil-Repellency]

0.20 Gram of the composition for a cosmetic was applied uniformly on a glass slide of 26 mm by 76 mm and dried at 150 degrees C. for 1 hour. Then, the glass slide was cooled to room temperature and a contact angle to water was measured by a contact angle meter to evaluate water repellency. Oil repellency was evaluated by measuring a contact angle to n-hexadecane instead of water in the same manner.

[Dispersibility]

20.0 Grams of the composition for a cosmetic and 80.0 g of decamethylcyclopentasiloxane were placed in a 200 cc flask and dispersed by a homodisper, ex Primix Corporation, for 15 minutes. The flask was left to stand still for 30 minutes and the state of dispersion was observed with the naked eye to evaluate the dispersibility.

[Storage Stability]

The composition for a cosmetic was placed in a sealed container and stored at 40 degrees C. for one week. The appearance of the composition was observed with the naked eye to evaluate the storage stability.

[Touch]

For evaluation of lightness and greasy touch, 20 panelists applied with the composition for a cosmetic on the backs of their hands and evaluated the touch of the composition according to the following criteria.

Lightness: The lightness of the composition for a cosmetic was evaluated in the scale of from 1 point (lightest) to 5 points (heaviest), and the points were averaged. An average score of 4 or larger was marked with "A"; 3 to less than 4, "B"; 2 to less than 3, "C"; and less than 2, "D".

Greasy touch: The greasy touch of the composition for a cosmetic was evaluated in the scale of from 1 point (lightest) to 5 points (heaviest), and the points were averaged. An average score of 4 or larger was marked with "A"; 3 to less than 4, "B"; 2 to less than 3, "C"; and less than 2, "D".

TABLE 1

| Evaluation item | Water repellency (deg) | Oil repellency (deg) | Dispersibility | Storage stability | Touch Light feeling | Touch Greasy touch |
|---|---|---|---|---|---|---|
| Example 1 | 102 | 40 | Good | Good | A | A |
| Example 2 | 100 | 36 | Good | Good | A | A |
| Example 3 | 104 | 38 | Good | Good | A | A |
| Example 4 | 101 | 37 | Good | Good | A | A |
| Comparative Example 1 | 100 | 36 | Good | Creep hardning | C | C |
| Comparative Example 2 | 106 | 41 | Settled | Oil separated | A | D |
| Comparative Example 3 | 88 | <20 | Good | Good | B | C |

As seen in Table 1, the present composition for a cosmetic has good storage stability, is a uniform paste and provides a significantly light and smooth feel.

Example 5

100.0 Parts by mass of the silicone polymer 2 prepared in Example 2 and 100.0 parts by mass of decamethylcyclopentasiloxane were mixed and dispersed, sufficiently kneaded under a shearing force with a three-roll mill, whereby the silicone polymer swelled with decamethylcyclopentasiloxane to prepare a composition for a cosmetic.

Example 6

Example 2 was repeated except that dimethylpolysiloxane (KF-96L-2cs) was used in place of decamethylcyclopentasiloxane to prepare a silicone polymer. 100 parts by mass of the silicone polymer and 100.0 parts by mass of KF-96L-2cs were mixed and dispersed, sufficiently kneaded under a shearing force with a three-roll mill, whereby the silicone polymer swelled with KF-96L-2cs to prepare a composition for a cosmetic. KF-96L-2cs provided the lighter feel and the lower tackiness to than decamethylcyclopentasiloxane.

The present composition for a cosmetic swells with low-viscosity silicone oil and has less tackiness, and therefore, yields a non-aqueous cosmetic which has lower tackiness and lighter feel.

When a certain composition for a cosmetic is added to an oil material for a cosmetic, tackiness may occur due to an interaction with water, such as emulsification. Therefore, tackiness in emulsion was evaluated in Examples 7 to 9 below.

Examples 7-8 and Comparative Examples 5-6

The components 1 to 6 were mixed according to the formulations shown in the following Table 1, and dispersed to uniformity, to which a solution consisting of components 7 to 10 was added while stirring with a disper to obtain a W/O type emulsion. The products obtained in Example 7 and Comparative Example 5 were W/O type milky lotions and the products obtained in Example 8 and Comparative Example 6 were W/O type creams.

TABLE 2

| | Components | Ex. 7 | Ex. 8 | Com. Ex. 5 | Com. Ex. 6 |
|---|---|---|---|---|---|
| | | | | (Mass %) | |
| 1 | Composition for a cosmetic prepared in Example 5 | 30.0 | 30.0 | — | — |
| 2 | Crosslinked dimetylpolysiloxane [1] | — | — | 30.0 | 30.0 |
| 3 | KSG-210 [2] | 3.0 | 3.0 | 3.0 | 3.0 |
| 4 | KF-6028 [3] | 2.0 | 2.0 | 2.0 | 2.0 |
| 5 | Decamethylcyclopentasiloxane | 25.0 | 5.0 | 25.0 | 5.0 |
| 6 | KF-96A-6cs [4] | 3.0 | 3.0 | 3.0 | 3.0 |
| 7 | 1,3-Butylene glycol | 3.0 | 3.0 | 3.0 | 3.0 |
| 8 | Sodium citrate | 0.2 | 0.2 | 0.2 | 0.2 |
| 9 | Sodium chloride | 0.5 | 0.5 | 0.5 | 0.5 |
| 10 | Purified water | 33.3 | 53.3 | 33.3 | 53.3 |
| | Total | 100.0 | 100.0 | 100.0 | 100.0 |

[1] KSG-16; pasty silicone composition swelled with decamethylcyclopentasiloxane, from Shin-Etsu Chemical Co., Ltd.
[2] Dimethicone/(PEG-10/15) crosspolymer, from Shin-Etsu Chemical Co., Ltd.
[3] PEG-9 Polydimethylsiloxyethyl Dimethicone, from Shin-Etsu Chemical Co., Ltd.
[4] Methylpolysiloxane (6cs), from Shin-Etsu Chemical Co., Ltd.

Example 9

Example 7 was repeated except that KF-6017 (PEG-10 dimethicone) was used in place of the component 4 (KF-6028) shown in Table 2 to obtain a W/O type milky lotion.

Example 10

Example 8 was repeated except that KF-6017 (PEG-10 dimethicone) was used in place of the component 4 (KF-6028) shown in Table 2 to obtain a W/O type cream.

The milky lotions and the creams prepared in Examples 7 to 10 and Comparative Examples 5 and 6 were subjected to an organoleptic evaluation on tackiness by 20 panelists. The tackiness in Examples 7 and 9 were evaluated, relative to that of the tackiness in Comparative Example 5; and in Examples 8 and 10, relative to that of Comparative Example 6. The results are as shown in Table 3.

TABLE 3

| | Tackiness improved | No change | Tackiness worsened (n) |
|---|---|---|---|
| Example 7 | 18 | 2 | 0 |
| Example 8 | 13 | 7 | 0 |
| Example 9 | 16 | 4 | 0 |
| Example 10 | 11 | 9 | 0 |

As seen in Table 3, it was confirmed that the cosmetic comprising the present composition for a cosmetic has reduced tackiness even in the emulsion with water, compared to the cosmetic comprising the conventional composition for a cosmetic.

Examples for cosmetics comprising the present composition for a cosmetic will be described below. The cosmetics had the formulations mentioned below.

Example 11

Wrinkle-Concealing Cream
The following components 1 to 8 were mixed and dispersed to uniformity, to which was added a uniform mixture of the following components 9 to 13 while stirring with a high speed stirring machine to obtain a wrinkle-concealing cream.

The wrinkle-concealing cream thus obtained was stable with time, did not show tackiness and spread smoothly on a skin.

|   | (Components) | Mass % |
|---|---|---|
| 1 | Composition for a cosmetic prepared in Example 5 | 22.0 |
| 2 | KSG-210 [2] | 3.0 |
| 3 | KF-6028 [3] | 1.0 |
| 4 | Decamethylcyclopentasiloxane | 23.0 |
| 5 | KF-96A-6cs [4] | 1.0 |
| 6 | KSG-15 [5] | 9.0 |
| 7 | KSP-101 [6] | 7.0 |
| 8 | Triethylhexanoin | 3.0 |
| 9 | 1,3-Butylene glycol | 3.0 |
| 10 | Sodium citrate | 0.2 |
| 11 | Sodium chloride | 0.5 |
| 12 | Purified water | 28.0 |
| 13 | Preservative | q.s. |

[5] Swelled product of crosslinked dimetylpolysiloxane, from Shin-Etsu Chemical Co., Ltd.
[6] Hybrid silicone powder, from Shin-Etsu Chemical Co., Ltd.

Example 12

Powder Foundation

The following components 4 to 10 were crushed and mixed to uniformity, to which was added and dispersed to uniformly a mixture of the following components 1 to 3 which had been mixed at room temperature. The product obtained was press molded by a mold to obtain a powder foundation. The powder foundation thus obtained gave refreshed feel, spread smoothly on a skin and was stable with time.

|   | Components | Mass % |
|---|---|---|
| 1 | Squalane | 1.0 |
| 2 | Composition for a cosmetic prepared in Example 3 | 4.0 |
| 3 | KF-96A-6cs [4] | 2.0 |
| 4 | Polyethylene powder | 1.5 |
| 5 | KMP-590 [7] | 4.5 |
| 6 | KSP-300 [8] | 3.0 |
| 7 | Barium sulfate | 10.0 |
| 8 | Hydrophobized sericite [9] | 40.0 |
| 9 | Hydrophobized talc [9] | 23.2 |
| 10 | Hydrophobized coloring agent [9] | 10.8 |

[7] Polymethylsylsesquioxane, from Shin-Etsu Chemical Co., Ltd.
[8] Phenyl-modified hybrid silicone powder, from Shin-Etsu Chemical Co., Ltd.
[9] Treated with KF-9909, from Shin-Etsu Chemical Co., Ltd.

Example 13

Conditioner Cream

The following components 1 to 6 were mixed and dispersed to uniformity, to which was added a uniform mixture of the following components 7 to 13 while stirring with a high speed stirring machine to obtain a conditioner cream. The conditioner cream thus obtained gave moisturized feel, did not show tackiness and spread smoothly on a skin.

|   | (Components) | Mass % |
|---|---|---|
| 1 | Composition for a cosmetic prepared in Example 5 | 4.0 |
| 2 | KSG-210 [2] | 4.0 |
| 3 | KF-6028 [3] | 0.2 |
| 4 | Squalane | 5.0 |
| 5 | Neopentylglycol diethylhexanoate | 7.6 |
| 6 | Dimethyl distearylammonium hectorite | 1.0 |
| 7 | KSG-15 [5] | 3.0 |
| 8 | Aqueous 2% solution of Xanthane gum | 4.0 |
| 9 | 1,3-Butylene glycol | 5.0 |
| 10 | Sodium citrate | 0.2 |
| 11 | Sodium chloride | 0.5 |
| 12 | Purified water | 65.2 |
| 13 | Preservative | q.s. |

Example 14

Suncut Milky Lotion

The following components 1 to 6 were mixed to uniformity, to which was added and emulsified a solution obtained by mixing the following components 9 to 12. The following components 7 and 8 were added to the emulsified product to obtain a suncut milky lotion. The suncut milky lotion thus obtained did not show tackiness or oiliness, spread smoothly on a skin and had good water resistance on a skin.

|   | (Components) | Mass % |
|---|---|---|
| 1 | KSG-210 [2] | 3.0 |
| 2 | KSG-15 [5] | 2.0 |
| 3 | KF-6028 [3] | 1.0 |
| 4 | Composition for a cosmetic prepared in Example 5 | 6.0 |
| 5 | Decamethylcyclopentasiloxane | 4.0 |
| 6 | Isotridecyl isononanoate | 4.0 |
| 7 | SPD-T5 [10] | 25.0 |
| 8 | SPD-Z5 [11] | 35.0 |
| 9 | Dipropylene glycol | 2.0 |
| 10 | Sodium citrate | 0.2 |
| 11 | Sodium chloride | 1.0 |
| 12 | Purified water | 16.8 |

[10] Titanium oxide fine powder dispersed, from Shin-Etsu Chemical Co., Ltd.
[11] Zinc oxide fine powder disperse, from Shin-Etsu Chemical Co., Ltd.

Example 15

Suncut Cream

The following components 1 to 8 were mixed to uniformity, to which was added a solution obtained by mixing the following components 9 to 12 and emulsified to obtain a suncut cream. The suncut cream thus obtained did not show tackiness or oiliness, spread smoothly, had good water resistance on a skin and was stable with time.

|   | (Components) | Mass % |
|---|---|---|
| 1 | KSG-210 [2] | 2.0 |
| 2 | KSG-15 [5] | 3.0 |
| 3 | KF-6028 [3] | 1.5 |
| 4 | Composition for a cosmetic prepared in Example 1 | 4.0 |
| 5 | Decamethylcyclopentasiloxane | 6.3 |
| 6 | Dimethyl distearylammonium hectorite | 1.2 |
| 7 | SPD-T5 [10] | 20.0 |
| 8 | SPD-Z5 [11] | 15.0 |
| 9 | 1,3-Butylene glycol | 5.0 |
| 10 | Sodium citrate | 0.2 |
| 11 | Sodium chloride | 0.5 |
| 12 | Purified water | 41.3 |

Example 16

Lipstick

The following components 1 to 11 were heated and mixed to uniformity, to which were added the following components 12 and 13 to form a uniformly mixture. The mixture was poured in a highly airtight container to obtain a lipstick. The lipstick thus obtained did not show tackiness or oiliness, was applied on a lip without smudge and stable with time.

| | Components | Mass % |
|---|---|---|
| 1 | Candelilla wax | 4.0 |
| 2 | Polyethylene | 2.0 |
| 3 | Microcrystalline wax | 3.0 |
| 4 | Composition for a cosmetic prepared in Example 2 | 8.5 |
| 5 | KP-561P [12] | 13.5 |
| 6 | KF-54 [13] | 20.0 |
| 7 | KP-545 [14] | 10.0 |
| 8 | KF-6105 [15] | 3.0 |
| 9 | Macadamia nut oil | 20.0 |
| 10 | Hydrogenated polyisobutene | 10.0 |
| 11 | Isotridecyl isononanoate | 6.0 |
| 12 | Coloring agent | q.s. |
| 13 | Mica | q.s. |

[12] Stearyl-modifled acrylic silicone resin, from Shin-Etsu Chemical Co., Ltd.
[13] Diphenyldimethicone, from Shin-Etsu Chemical Co., Ltd.
[14] D5 solution of acryl silicone, from Shin-Etsu Chemical Co., Ltd.
[15] Polyglycerin/alkyl co-modified branched silicone, from Shin-Etsu Chemical Co., Ltd.

Example 17

W/O Type Liquid Foundation

The following components 1 to 10 were mixed to uniformity, to which was added a solution obtained by mixing the following components 11 to 16 and emulsified to obtain a liquid foundation. The W/O type liquid foundation thus obtained did not show tackiness or oiliness, spread smoothly on a skin and stable with time.

| | Components | Mass % |
|---|---|---|
| 1 | KSG-210 [2] | 3.5 |
| 2 | KSG-15 [5] | 3.0 |
| 3 | KF-6028 [3] | 3.0 |
| 4 | Decamethylcyclopentasiloxane | 9.0 |
| 5 | Composition for a cosmetic prepared in Example 2 | 4.0 |
| 6 | KF-96A-6cs [4] | 1.0 |
| 7 | Trioctanoine | 7.0 |
| 8 | KSP-100 [16] | 2.0 |
| 9 | KF-7312J [17] | 2.0 |
| 10 | Hydrophobized coloring agent [9] | 10.0 |
| 11 | 1,3-Butylene glycol | 5.0 |
| 12 | Xanthane gum | 0.1 |
| 13 | Sodium citrate | 0.2 |
| 14 | Sodium chloride | 0.5 |
| 15 | Preservative | q.s. |
| 16 | Purified water | 49.4 |

[16] Hybrid silicone powder, from Shin-Etsu Chemical Co., Ltd.
[17] D5 solution of trimethylsiloxy silicate, from Shin-Etsu Chemical Co., Ltd.

Example 18

O/W Type Cream

The following components 1 to 3 were mixed to uniformity, and then gradually added to a uniformly dispersed mixture of the following components 4 to 10 while stirring and emulsified to obtain an O/W type cream. The O/W type cream thus obtained did not show tackiness or oiliness and gave refreshed feel.

| | Components | Mass % |
|---|---|---|
| 1 | KSG-15 [5] | 8.0 |
| 2 | Decamethylcyclopentasiloxane | 10.0 |
| 3 | Composition for a cosmetic prepared in Example 6 | 30.0 |
| 4 | 1,3-Butylene glycol | 3.0 |
| 5 | KF-6100 [18] | 0.6 |
| 6 | KF-6104 [19] | 0.3 |
| 7 | SIMULGEL600 [20] | 0.6 |
| 8 | Aqueous 1% solution of Sodium chloride | 8.0 |
| 9 | Purified water | 26.5 |
| 10 | Aqueous 5% solution of AristoflexAVC [21] | 13.0 |

[18] Polyglycerin-modified branched silicone with a medium HLB, from Shin-Etsu Chemical Co., Ltd.
[19] Polyglycerin-modified branched silicone with a high HLB, from Shin-Etsu Chemical Co., Ltd.
[20] Acrylic thickening agent mixture, from SEPIC Co., Ltd.
[21] Water-soluble acrylic polymer, from Clariant.

INDUSTRIAL APPLICABILITY

The present invention provides a composition for a cosmetic comprising low-viscosity silicone oil and a silicone polymer which has swellability with the low-viscosity silicone oil. The present composition for a cosmetic can provide a cosmetic which shows lower tackiness, is stable with time, spreads smoothly and give a smooth feel on a skin, is easily prepared and has good storage stability.

The invention claimed is:

1. A cosmetic composition comprising:

a fluorine-containing silicone polymer having a three-dimensional, cross-linked structure, prepared by addition polymerizing the following (A), (B) and (C) and containing 10 to 30 mass % of the fluorine atoms, relative to a total mass of (A) to (C), (A) a vinyl group-containing organopolysiloxane represented by the following formula (1):

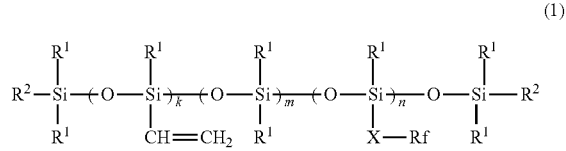

(1)

wherein Rf is a perfluoroalkyl group having 1 to 10 carbon atoms or a perfluoropolyether group having 3 to 30 carbon atoms; $R^1$ is, independently of each other, a monovalent hydrocarbon group having 1 to 10 carbon atoms without any aliphatic unsaturated bond; $R^2$ is, independently of each other, a vinyl group or a monovalent hydrocarbon group having 1 to 10 carbon atoms without any aliphatic unsaturated bond; k is an integer of 0 to 10, provided that the organopolysiloxane has at least two, per molecule, vinyl groups bonded to silicon atoms; X is a divalent organic group, m is an integer of 0 to 200, and n is an integer of 0 to 100, (B) an organohydrogenpolysiloxane represented by the following formula (2):

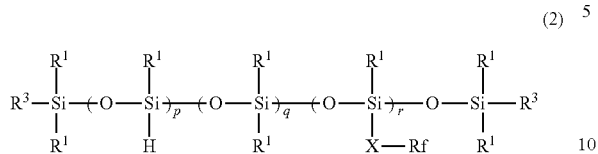

wherein $R^3$ is, independently of each other, a hydrogen atom or a monovalent hydrocarbon group having 1 to 10 carbon atoms without any aliphatic unsaturated bond; p is an integer of 0 to 10, provided that the organopolysiloxane has at least two, per molecule, hydrogen atoms bonded to silicon atoms; q is an integer of 0 to 200; r is an integer of 0 to 100, provided that n in formula (1) and r in formula (2) are not simultaneously zero; and at least either one of the number of the vinyl groups bonded to silicon atoms in formula (1) or the number of the hydrogen atoms bonded to silicon atoms in formula (2) is at least three; and Rf, X, and $R^1$ are as defined above, and (C) an organopolysiloxane having a reactive group on one end alone and represented by the following formula (3),

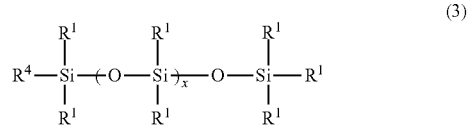

wherein $R^4$ is a hydrogen atom or a vinyl group, x is an integer of 0 to 100, and $R^1$ is as defined above, and further comprising (D) a low viscosity silicone oil with a dynamic viscosity of 50 mm²/s or less at 25 degrees C., wherein said composition is suitable for use as a cosmetic.

2. The cosmetic according to claim 1, wherein the cosmetic further comprises a branched silicone activator.

3. The cosmetic according to claim 1, wherein the composition is in a state of fine powder, paste or grease.

4. The cosmetic according to claim 3, wherein the cosmetic further comprises a branched silicone activator.

\* \* \* \* \*